United States Patent [19]

Paradis

[11] Patent Number: 4,886,356

[45] Date of Patent: Dec. 12, 1989

[54] DETECTOR CELL FOR LIQUID CHROMATOGRAPHY

[75] Inventor: Roland C. Paradis, Newtown, Conn.

[73] Assignee: The Perkin-Elmer Corporation, Norwalk, Conn.

[21] Appl. No.: 176,524

[22] Filed: Apr. 1, 1988

[51] Int. Cl.[4] .......................................... G01N 21/05
[52] U.S. Cl. ..................................... 356/246; 356/440
[58] Field of Search ....................... 356/246, 410, 440; 250/343, 373, 576

[56] References Cited

U.S. PATENT DOCUMENTS

| | | | |
|---|---|---|---|
| 3,740,158 | 6/1973 | Bellinger et al. | 356/246 |
| 4,121,859 | 10/1978 | DeMay, II | 285/93 |
| 4,192,614 | 3/1980 | DeMay, II et al. | 356/410 |
| 4,589,477 | 5/1986 | Scott | 165/66 |
| 4,598,765 | 7/1986 | Atwood et al. | 165/66 |
| 4,747,687 | 5/1988 | Hoppe et al. | 356/246 |

Primary Examiner—Davis L. Willis
Assistant Examiner—Matthew W. Koren
Attorney, Agent, or Firm—Herbert S. Ingham; Edwin T. Grimes; Thomas P. Murphy

[57] ABSTRACT

A detector cell assembly for use in a spectrophotometer comprises a thermally insulating body having a bore with open ends therethrough and transparent windows closing the ends of the bore. An inlet passage and an outlet passage open into the bore adjacent the opposite ends thereof for flowing fluid therethrough. The body has size defined by an outer surface spaced laterally from the bore by a distance of at least about two times the bore diameter. Preferably the thermally insulating body is polymeric and has an outwardly facing annular surface respectively encircling each end of the bore approximately normal thereto and in contact with a corresponding surface on the respective window. A spring urges each respective transparent window against the respective annular surface to effect a fluid seal between the body and each window.

8 Claims, 1 Drawing Sheet

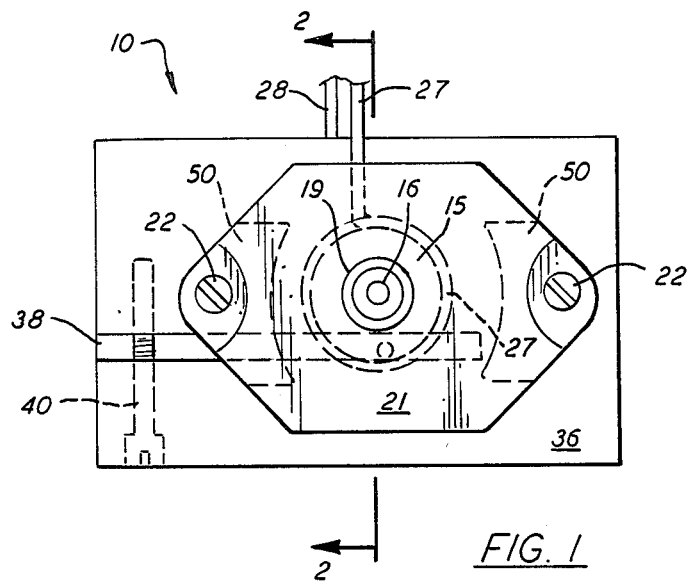
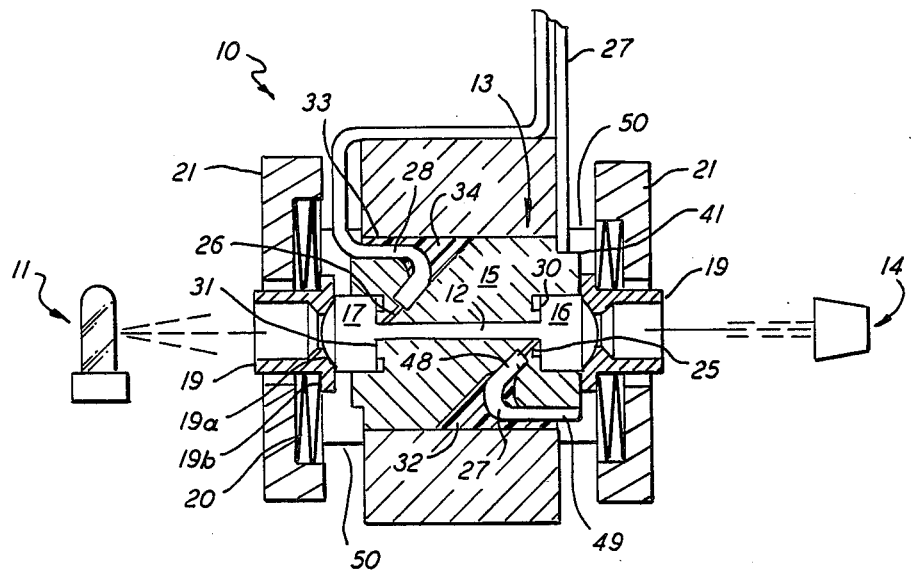

DETECTOR CELL FOR LIQUID CHROMATOGRAPHY

The present invention relates to detectors for spectrophotometers and particularly to a detector for a spectrophotometer of the flow-through type utilizing variable wavelength radiation for liquid chromatography.

BACKGROUND OF THE INVENTION

In the subject type of spectrophotometers for liquid chromatography (LC) a substance whose quantitative presence in a sample is to be determined is dissolved in a suitable carrier solvent, separated in an LC column and flowed through a detector cell which has end windows through which ultraviolet or visible light radiation is directed. Radiation exiting from the cell falls on a photodetector whose output is recorded by suitable instrumentation which is calibrated to indicate the amount of radiation absorbed by the fluid flowing through the cell. Absorbance is customarily indicated by a graph continuously recorded on a strip chart by a pen recorder. The quantitative presence of a substance of interest is determined by measuring the area under the graph peaks which represent the amount of radiation of a particular wavelength that is absorbed, particular materials being identified by particular wavelengths characteristically absorbed by them.

The sensitivity of a spectrophotometer detector cell is a function particularly of the stability of the base line of the graph; the graph base line is established by the absorbance of the solvent used, and will change in relation to any change in the refractive index of the solvent, which in turn will be changed by a change in the temperature of the solvent in the cell. When the baseline changes, the true peak area can not be measured accurately and the peaks themselves become less clearly defined and hence difficult to identify and measure with any reliable degree of accuracy. The sensitivity of the instrument which is rather limited in the best circumstance when the index of refraction of the solvent remains constant (i.e. when flow noise is at a minimum) is disproportionally reduced by any change in temperatures of the solvent, thus altering its index of refraction and increasing flow noise.

U.S. Pat. No. 4,192,614 discloses a spectrophotometer cell assembly including a cell defined by a bore through a body and closed at the ends by radiation transparent windows with inlet and outlet passages through the body to the bore, so that radiation passed through the sample fluid flowing through the bore is detected by a photodetector. The body, which is expressly disclosed to be made of a thermally conductive material, is a large thermal mass in relation to the volume of the cell. A tubular inlet conduit, also made of a thermally conductive material, wraps around the body and connects to the inlet passage so that fluid flowing into the bore will tend to equilibrate and reach a stable temperature due to the heat sink effect of the body and conduit, thereby stabilizing the refractive index of the fluid in the bore and enhancing the sensitivity of the photodetection.

U.S. Pat. Nos. 4,598,765 and 4,589,477 also involve such apparatus and are similarly concerned about equilibrating temperature. Each of the three aforementioned patents teaches a complex means for heat exchanging with respect to the inlet conduit and a thermally conducting housing that forms the cell. Because of such construction with corrosion resistant metal cells with relatively small size and a requirement for precision, the prior art apparatus is quite difficult and expensive to make. Problems with the equilibration construction also include fluid mixing in the inlet tube length causing increased bandwidth of a fluid sample, and incomplete equilibration for high fluid flow rates. Also, a long inlet tube associated with the heat exchanger is more susceptible to blockage.

Reliability problems have been encountered in sealing the cells. A transparent window such as an optical lens must be sealed into the metal cell. This has been effected by a gasket such as described in U.S. Pat. No. 4,121,859. A specially angled surface in the cell body is also required, further adding to cost. The gasket has been prone to distorting or breaking thus causing blockage of fluid flow and optical path.

Prior art LC detectors, as represented by the aforementioned patents (which are assigned to the same assignee as the present invention), have become quite accurate. However, a significant requirement for further improvement exists.

SUMMARY OF THE INVENTION

Therefore, objects of the present invention are to provide a spectrophotometer detector cell for liquid chromatography that is more accurate and reliable than previously known types of such detector cells; to provide such a detector cell without a requirement for heat exchange between the liquid inlet tube and a heat conducting cell body; to provide such a detector cell that is considerably easier and less expensive to fabricate; and to provide such a detector cell without gasket sealing problems associated with optical windows associated with the prior art.

The foregoing and other objects of the present invention are achieved by a detector cell assembly for use in a spectrophotometer including a source of radiation and a photodetector spaced from the source, the cell assembly being positionable between the radiation source and the photodetector. The cell assembly comprises a body having a bore therefore with open ends. Radiation transparent windows respectively close the ends of the bore. An inlet passage and an outlet passage open into the bore respectively adjacent the opposite ends thereof for flowing fluid therethrough. According to the present invention the body is thermally insulating to the fluid flowing in the bore. The body should have a size defined by an outer surface spaced laterally from the bore by a radial distance of at least about two times the bore diameter. Preferably the thermally insulating body is polymeric, and the transparent windows are optical lenses.

According to a preferred embodiment, the polymeric body has an outwardly facing annular surface respectively encircling each end of the bore approximately normal thereto and in contact with a corresponding surface on the respective window. The cell assembly further comprises urging means for urging each respective transparent window against the respective annular surface to effect a fluid seal between the polymeric body and each transparent window.

BRIEF DESCRIPTION OF THE DRAWINGS

FIG. 1 is an end elevation of a detector cell assembly embodying the present invention.

FIG. 2 is a sectional view taken along the lines 2—2 of FIG. 1, but shown in combination schematically with a source of radiation and photodetector of a spectrophotometer.

DETAILED DESCRIPTION OF THE INVENTION

Referring to FIGS. 1 and 2 of the drawing, a detector cell assembly 10 in accordance with the invention may be made as a separate unit assembly 13 adapted to be inserted as the detector cell in a multi purpose spectrophotometer, or it may be built in. In the embodiment shown the unit assembly 13 is shown and described as a composite unit adapted to be inserted in a multipurpose spectrophotometer instrument. The unit is inserted in position for radiation from a spectrophotometer source 11 (FIG. 2) of radiation to pass through a windowed cell bore 12 of detector assembly 13 and impinge on the photosensitive surface of a photodetector 14. Photodetector 14 produces output signals proportional to the radiation received, the signals thus being proportional to the amount of light absorbed by a sample fluid flowing through cell bore 12. Signals from photodetector 14 are processed by means well known in the art to provide an analysis in interpretable form, such as a continuous graph produced by a pen recorder.

Source 11 is suitably a deutrium arc lamp and the particular wavelength of the radiation to be applied to cell bore 12 is suitably selected by a monochromator or filter (not shown) in the path of the radiation from source 11 to cell bore 12. End windows 16,17 which are preferably optical lenses, are each made of a suitable radiation transparent material such as quartz and are fitted in a coaxial counterbore of cell body 15 and sealed over the ends of cell bore 12. The windows are sealed in place by means of a pressure tight seal to be described below.

A body 15 of assembly 13 has an inlet passage 25 and an outlet passage 26 drilled through body 15 to open into bore 12 adjacent enlarged end portions of the cell bore 12 where lenses 16,17 are disposed, respectively. As indicated in FIG. 2, the enlarged end portions of cell bore 12 are suitably provided by further counterboring each end of the bore to provide a boss 30,31 encircling each end of bore 12 in the counterbore hole.

At their outer ends, inlet and outlet passages 25,26 are connected respectively to an inlet tube 27 and to an outlet tube 28 which are made of suitably corrosion resistant material. Aluminum or brass might in some cases be used for tubes 27,28, but stainless steel or titanium or the like should be used to enable the instrument to be used for highly corrosive materials. Inlet tube 27 is receptive of sample liquid flow, typically a solvent and with a dissolved sample. Outlet tube 28 suitably leads to a waste pipe or waste container (not shown).

According to the present invention body 15 is formed of a thermally insulating material, preferably a high strength, hard polymer that is also chemically resistant to any corrosive fluid likely to be passed through the cell. Suitable polymers for the body are Vespel (TM) polyamid from DuPont and Torlon (TM) 4203 polyamid-imid from Amoco. A preferred method of construction is to drill respective holes for the tubes in alignment with passages 25,26, and cut slots 32,33 in the outer surface of the body from each hole to the corresponding end face of the body. Each tube 27,28 is pre-bent with an inner portion 48 and an outer portion 49, and fitted into its hole and slot, where it is held in place with a suitable cement 34, such as epoxy, which is also chemical resistant and preferably thermally insulating. The hole may be slightly larger than the tube to accommodate the cement. A suitable epoxy is EP41HT from Master Bond, Inc.

Unit assembly 13 comprises body 15 with the inlet and outlet tubes 27,28 cemented in place. Referring to FIGS. 1 and 2, body 15 is fitted into a holder 36 which has a slot 38 and a screw 40 to clamp body 15 in place. Tubes 27,28 are curved as required to be led away from cell 10. Tube 27 is shown curved half way around a shoulder cut 41 on the end of body 15, so the tubes can be led away together. In the example of FIGS. 1 and 2 the unit assembly 13 is retained in a holder of a type depicted as 36. However an advantage of the construction of unit 13 is interchangability into different LC instrument configurations. Thus holder 36 may be replaced by any other convenient shape or may be integrated into the instrument.

With body 15 being formed of thermally insulating material it is not necessary for inlet tube 27 to be associated with any heat exchanging means with the body; the tube is merely led along any convenient path, and either tube may be selected for the inlet except it is customary for the inlet to be from the bottom of bore 12 and the outlet from the top. The Z-shaped path of the inlet tube, bore and outlet tube is convenient and preferred. To effect thermal insulation, the body should have some significant wall thickness radially outward of the bore. Thus the lateral (radial) distance from the bore to the outer surface of the body should be at least two, and preferably five, times the bore diameter. A 12.7 mm diameter body is suitable for a 1.0 mm bore. In consequence of the thermally insulating body the sample fluid flowing continuously through the cell bore 12 will be at a substantially uniform temperature; the refractive index of the solvent thus remains substantially constant, thereby eliminating flow noise so as to enhance sensitivity and accuracy of the measurements being taken.

Continuing with FIG. 2, lenses 16,17 are each held in place against corresponding boss 30,31 by a bushing 19 of brass or the like, having an inward flange surface 19a bearing against the outer circumferential surface of the lens and an outward flange 19b. Three or more Bellville spring washers 20 are placed around each of the bushings 19 and are held under compression against outward flange 19b by retaining clamps 21 which are held in place on the body by screws 22 (FIG. 1). The retaining clamps each have a pair of supports 50 cast therein and located under the screws to position and space the clamps on holder 36 for correct compression of springs 20.

Inward flange surface 19a mates with the convex outer surface of the corresponding lens such as to provide a radially inward component to the imaging force. Thus, the counterbore in which the lens rests generally locates the lens, and bushing 19 self centers on the lens and applies the axial sealing force toward the center of curvature of the lens. Also, there is no corresponding counterbore for the lens in the bushing, as in prior art LC instruments, to conflict with the centering action of inward flange 19a.

The low thermal conductivity of the body material, which is less than about 2 BTU-in/hr ft$^2$°F. for the preferred polymers, has made it possible to eliminate the requirement of heat exchangers for cells. Heretofore, when a column effluent entered the hot or cold stainless steel cell, heat transfer took place between them altering the refractive index of the separated solvent giving inconsistent readouts. Therefore, heat exchangers were designed to bring the column effluent temperature to the cell temperature before it entered the cell bore. The polymer body 15 of the present invention neither conducts nor releases heat to the flowing solvent, thereby maintaining stability for the given sample and obviating the necessity of heat exchangers. Heat exchangers of the prior art have contributed greatly to the cost of flow cells, and, at the same time, have decreased their efficiency by increasing instrumental bandwidth because the longer inlet tube allowed undesirable mixing in the fluid. Surprisingly the detector of the present invention shows improved bandwidth and little sensitivity to changes in fluid flow rate. Yet another advantage is low replacement cost, which is made possible in part by the elimination of the heat exchanger which had to be made part of the unit assembly.

It has further been found that if the body is formed of a polymer with selected characteristics, in cooperation with the lenses being urged against the body with a certain force and a certain contact area, a gasket is not necessary between each lens and the body. Assembly 10 with spring washers 20 should urge each window lens with a force of between about 30 pounds ($1.3 \times 10^7$ dynes) and about 40 pounds ($1.8 \times 10^7$ dynes). Protruding boss 30,31 at each end of the body defines an outwardly facing annular surface respectively encircling the bore approximately normal thereto, the surface being in matching contact with the corresponding surface of the lens (the boss surfaces are also shown at 30,31 respectively). The surfaces should each have a contact area on the lens of between about 0.006 in$^2$ (3.87 mm$^2$) and about 0.008 in$^2$ (5.16 mm$^2$). With a selected polymeric, thermally insulating material having sufficiently low creep and high modulus for each boss to deform between about $1.4 \times 10^{-4}$ in. ($3.5 \times 10^{-3}$ mm) and about $0.5 \times 10^{-4}$ in. ($1.3 \times 10^{-3}$ mm), excellent sealing is effected for high pressure liquid flow in the cell, vis. a pressure of at least 3600 psi (248 dynes/cm$^2$).

Elimination of the separate gasket and its special seat, required with prior art detector cells, has improved cell reliability considerably. Seating is reliable, and there are no longer occurrences of a gasket deforming out of place or breaking to interfere with fluid flow or optical path. Assembly time is decreased since gasket alignment is eliminated.

An additional benefit of the detector of the present invention is a substantial reduction in cost and manufacturing reliability. The cell is quite small, and requires precision. For example bore 12, is 1.0 cm long and 1.0 mm diameter, and inlet and outlet passages 25,26 are 0.45 mm diameter. Fabrication from stainless steel including tube attachment is quite difficult and labor intensive, and there has been a high scrap rate due to tool breakage, especially small drills. These problems are even more pronounced with titanium that is necessary for biotech fluids. Use of the polymer body, particularly with the aforementioned construction with cementing in the tubes and omission of gaskets, is a major improvement.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

What is claimed is:

1. A detector cell assembly for use in a spectrophotometer including a source of radiation and a photodetector spaced from the source, the cell assembly being positionable between the radiation source and the photodetector and comprising:
   a body having a bore therethrough with open ends and radiation transparent windows respectively closing the ends of the bore and further having an inlet passage and an outlet passage opening into the bore respectively adjacent the opposite ends thereof for flowing fluid therethrough, an inlet tube receptive of sample liquid flow and connecting with the inlet passage, and an outlet tube connecting with the outlet passage; wherein
   the body is thermally insulating to the fluid flowing in the bore, the inlet passage, the outlet passage and the bore are arranged in a Z-shaped pattern in the body, the inlet and outlet tubes each is sealingly mounted in the body with polymer cement, each tube has an inner portion aligned and connected with the corresponding passage and leading to a point of intersection with the outer surface of the body, the outer surface of the body has slots therein extending from each point of intersection to a corresponding end of the body, and each tube has an outer portion curved from the inner portion to lie in the corresponding slot.

2. A detector cell assembly according to claim 1 wherein the thermally insulating body has a size defined by an outer surface spaced from the bore by a radial distance of at least about two times the bore diameter.

3. A detector cell assembly according to claim 1 wherein the thermally insulating body is polymeric.

4. A detector cell assembly according to claim 3 wherein the polymeric body has an outwardly facing annular surface respectively encircling each end of the bore approximately normal thereto and in contact with a corresponding surface on the respective window, and the cell assembly further comprises urging means for urging each respective transparent window against the respective annular surface to effect a fluid seal between the polymeric body and each transparent window.

5. A detector cell assembly for use in a spectrophotometer including a source of radiation and a photodetector spaced from the source, the cell assembly being positionable between the radiation source and the photodetector and comprising:
   a polymeric body having a bore therethrough with open ends and radiation transparent windows with substantially flat surfaces respectively closing the ends of the bore and further having an inlet passage and an outlet passage opening into the bore respectively adjacent the opposite ends thereof for flowing fluid therethrough; wherein
   the body is thermally insulating to the fluid flowing in the bore, the polymeric body has an outwardly facing annular surface defined on a protruding boss respectively encircling each end of the bore approximately normal thereto and in contact with a corresponding substantially flat surface on the respective window, and the cell assembly further comprises urging means for urging each respective transparent window against the respective protruding boss to effect a seal between the polymeric body and each transparent window.

6. A detector cell assembly according to claim 5 wherein the urging means is such as to urge each transparent window with a force of between about 30 pounds ($1.3 \times 10^7$ dynes) and about 40 pounds ($1.8 \times 10^7$ dynes), each annular surface has a contact area on the respective transparent window between about 0.006 in$^2$ and about 0.008 in$^2$ and the polymeric insulating material has sufficiently low creep and high modulus for each boss to deform between about $0.5 \times 10^{-4}$ in ($1.3 \times 10^{-3}$ mm) about $1.4 \times 10^{-4}$ in ($3.5 \times 10^{-3}$ mm) and by the respective transparent window under the urging means.

7. A detector cell assembly according to claim 5 wherein the body is polymeric with a counterbore at each end coaxial with the bore, each window is an optical lens fitted into a respective counterbore and having a convex circumferential outer surface with a center of curvature, and the urging means includes a bushing having an inward flange surface bearing against the convex outer circumferential surface of the lens such as to provide radial forces directed toward the center of curvature such as to uniformly distribute a sealing force between the lens and the annular surface.

8. A detector cell assembly according to claim 5 wherein each transparent window is an optical lens.

* * * * *